United States Patent [19]

Butera

[11] E Re. 31,232

[45] Reissued May 10, 1983

[54] CALIBRATED OIL BURNER FILTER PAPER

[76] Inventor: Anthony W. Butera, 112 Tuthill St., Port Jefferson, N.Y. 11777

[21] Appl. No.: 241,138

[22] Filed: Mar. 6, 1981

Related U.S. Patent Documents

Reissue of:

[64] Patent No.: 4,170,127
Issued: Oct. 9, 1979
Appl. No.: 890,784
Filed: Mar. 27, 1978

U.S. Applications:

[63] Continuation-in-part of Ser. No. 714,951, Sep. 3, 1976, Pat. No. 4,095,729.

[51] Int. Cl.[3] ..... G01N 21/00

[52] U.S. Cl. ..... 73/28; 116/214; 116/DIG. 14; 283/1 A; 356/438

[58] Field of Search ..... 116/214, DIG. 22; 73/64, 28; 356/438, 243, 38; 283/1 A

[56] References Cited

U.S. PATENT DOCUMENTS

| | | | |
|---|---|---|---|
| 1,151,395 | 8/1915 | Roberts | 356/438 X |
| 2,380,244 | 7/1945 | Jones et al. | 356/243 X |
| 2,667,779 | 2/1954 | von Brand | 73/28 |
| 2,675,697 | 4/1954 | Quynn et al. | 73/28 |
| 2,722,998 | 11/1955 | Hall | 73/28 X |
| 2,826,073 | 3/1958 | Huyck et al. | 116/DIG. 14 |
| 3,464,257 | 9/1969 | Schreiber et al. | 73/28 |
| 3,654,801 | 4/1972 | Keefer et al. | 356/38 |
| 3,770,356 | 11/1973 | Kimura | 356/38 X |
| 3,779,650 | 12/1973 | Crowley | 356/438 |
| 3,859,842 | 1/1975 | Bosch | 73/28 |
| 3,863,490 | 2/1975 | Blunck et al. | 73/28 |
| 4,079,622 | 3/1978 | Cocola et al. | 73/28 |
| 4,095,729 | 6/1978 | Butera | 225/42 |

FOREIGN PATENT DOCUMENTS

| | | | |
|---|---|---|---|
| 941520 | 3/1956 | Fed. Rep. of Germany | 73/64 |

OTHER PUBLICATIONS

Publ. "Standard Test" of Smoke Density in Flue Gases from Distillate Fuels, (No. D 2156), Aug. 31, 1965, ASTM Z11, 182-1965.

*Primary Examiner*—Daniel M. Yasich

[57] ABSTRACT

This invention relates to a calibrated oil burner filter paper on which is imprinted or otherwise processed a pre-selected geometrically shaped standard gray smoke scale and its integral use with an oil burner smoke tester and dispenser to provide a paper record for a quick and accurate visual analysis of the smoke density of a test smoke spot of the flue gases from burning distillate fuels, and also in the subsequent determination of the "Smoke Spot Number" of the flue gases by visually matching the shade of the test smoke spot lying in juxtaposition with the most like shade of a sector of the said imprint of a pre-selected shaped standard smoke test scale.

6 Claims, 4 Drawing Figures

CALIBRATED OIL BURNER FILTER PAPER

Matter enclosed in heavy brackets [ ] appears in the original patent but forms no part of this reissue specification; matter printed in italics indicates the additions made by reissue.

*This application is a continuation-in-part of Ser. No. 714,951, filed Sept. 3, 1976, now patent No. 4,095,729.*

BACKGROUND OF INVENTION

Particular difficulty has been found in the present method of spot-testing the smoke content in the flue pipe of an oil burner. Namely, the filter paper in common use today is in strip form and obtained by the technician tearing off a useable piece of paper from a serrated sheet to form a useable strip. Herein lies one of the difficulties. Usually the technician making the test has either serviced the oil burner or has made an inspection. As a result his hands are quite often covered by a quantity of soot, oil, dust, or other matter generally found around an oil burner. Hence, the moment he selects a filter strip he imparts a print or smudge from his hands on the filter paper even before he makes a test. This contamination can degrade the test data and lead to an erroneous conclusion. Also, the concept of placing a small strip of limp paper in a narrow slot is awkward and difficult and often falls out of the tester and on the floor where it is further dirtied.

Another dificulty of importance is that after a smoke spot test has been made, the test strip of filter paper must be removed from the spot tester and physically placed next to a standard smoke scale for inspection. In so doing, the test paper has to be handled again and can be easily dropped, further contaminating the results. Since several tests are usually made on one strip, any disorientation of the test strip by being dropped can cause confusion as to which was the first or the last test.

SUMMARY OF THE INVENTION

The object of my invention is to provide by proximity on a filter paper an immediate means to compare and identify a sample smoke test along side of a built in imprint or otherwise processed Oil Burner Smoke Scale, without having to remove the filter paper from the tester to make a similar comparison against a remotely located reference smoke scale, as well as to provide a continuous supply of clean filter paper calibrated, indexed and repeated for use with an Oil Burner Test Dispenser such as described in patent application Ser. No. 714,951, [now U.S. Pat. No. 4,095,729, filing date Aug. 5, 1976.] *filed Sept. 3, 1976, now Patent No. 4,095,729.*

Also, the novelty of this invention provides for an initial alignment of the calibrated oil burner filter paper in a smoke spot tester such that the test smoke spot of the flue gases of an oil burner occur in the midst of a shaped gray smoke scale consisting of a geometric form. As a result of the test smoke spot lying in juxtaposition with a shaped gray smoke scale, an easy and quick and accurate match of the shade of the test smoke spot can be made with a like most shade of a numbered segment of the standard smoke scale. This number is designated as the "Smoke Spot Number". This "Smoke Spot Number" is very important in determining the optimum air-fuel ratio and maximum efficiency for an oil burner. This optimization is done on a trial basis during the burning of a distillate fuel, where the sequence is first make an air adjustment, then perform a test smoke spot, then make an analysis of the test smoke spot, and finally, repeat the sequence until an optimum "Smoke Spot Number" is achieved. Usually several tests are made before an optimum air-fuel adjustment has been reached.

The advantage of this new concept over any previous field type method is that the test smoke spot occurs in the midst of the shaped standard smoke scale and the results are easy to analize and are accurate. This feature is time saving and provides a new process for a fast turn around between tests. It is in itself, a great improvement over any previous method of obtaining a test smoke spot. This should decrease the time and number of adjustments and encourage an oil burner technician to use and to more heavily rely upon test instruments for the final adjustment and analysis of an oil burner to obtain clean burning and maximum efficiency.

DETAILED DESCRIPTION OF THE INVENTION

Figure 1:
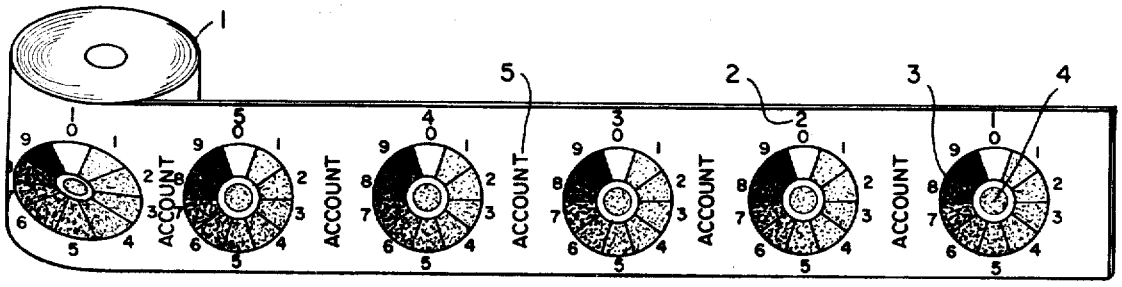
FIG. 1 is a detailed view of the circular shaped calibrated gray smoke scale. The smoke scale is evenly divided and is numbered consecutively from 0 to 9. Each number is expressed as a "Smoke Spot Number". Also, each sector of the smoke scale is to vary through grades of gray and conforms to the specification in the 1974 ANNUAL BOOK OF ASTM STANDARDS, PART 24, Petroleum Products and Lubricants (11), pages 186–187, published by the American Society for Testing and Materials, 1916 Race St. Philadelphia, Pa. 19103, Designation D 2156–65. The numbers 1 through 5 on top of the filter paper form a sequence and repeat to provide for identification, record keeping and future reference. The word Account provides space to label the smoke test with the customers identity.

These features can be more clearly understood when considered in conjunction with the accompanied drawings, FIGS. (1), (2), (3), and (4). The filter paper (1) is to be provided in roll form or in lengths as will be accepted by different size smoke paper dispensers of smoke testers. The index numbers (2) are for the purpose of aligning the space for the test smoke spot (4) in a tester and also for identification. The gray scale (3) is repeated continuously along the roll while the index numbers (2) from one to five constitutes a set which repeats. The numbers which form a set are not limited to five but have been arbitrarily chosen as such for convenience. Space is also provided to identify the test with an account. (5).

A typical example of the use of the invention is as follows: The paper (1) would be stored in a dispenser (Ref. pat. app. Ser. No. 714,951) and the first test would be made ready by moving the test paper until one of the index numbers (2) would appear over the centerline and the probe of the particular smoke tester. After the sample of flue gas was taken, the next test would be made ready by pulling the test paper to the next built in index number (2), while in so doing the first test would now be out from the tester and in view of analysis. The sample smoke spot (4) would appear in the vicinity of the calibration scale (3) ready for instant comparison and determination of the "Smoke Spot Number" content of the flue gas. The advantage that each test uses a fresh and clean built in scale (3) emerging from a dispenser without being handled is obvious. Also, the account (5) can be labeled for identification for future reference.

The filter paper (1), under use has the characteristics of a CHROMATOGRAPH FILTER PAPER. However, filter paper or filtering media of different characteristics can be used. The novelty is that the analysis of the flue smoke test can be preformed next to built in repeating calibration gray scales (3) and repeating set of index numbers (2) without having to align and compare the test results with a separate or remotely located Oil Burner Smoke Scale. The gray scale (3) located on the filter paper varies progressively in density from zero (0) to nine (9) and conforms to known standard gray scales as shown in the article titled "Standard Method of Test for Smoke Density in the Flue Gases from Distillate Fuels, ASTM Designation D 2156–65 (Reapproved 1970)", appearing in the 1974 ANNUAL BOOK OF ASTM STANDARDS, PART 24, pages 186–187 and published by the American Society for Testing and Materials, 1916 Race St. Philadelphia, Pa. 19103. The scale (3) also conforms with deposits left from flue test volumes of 2250 cubic inches per square inch of filtering area and are in terms of "Smoke Spot Number". Each smoke tester that uses this calibrated filter paper or other calibrated filter paper, or filter media of other characteristics using this principle of a built in calibrated scale as well as other smoke testers working on the principle of sampling a volume of flue gas, will require it's own calibration to match the ASTM D 2156–63 T Specification. Furthermore, this invention provides a space to identify the account (5). Prior to this invention, the method of comparison was to remove the test paper (void of any reference information) from the tester and physically transport it and align it with the smoke spot with a separate reference for analysis. The advantage of having the smoke test deposit lie next to a built in scale of reference are readily obvious when compared to the aformentioned method of handling the test results by an official or technician with dirty hands.

Figure 2:
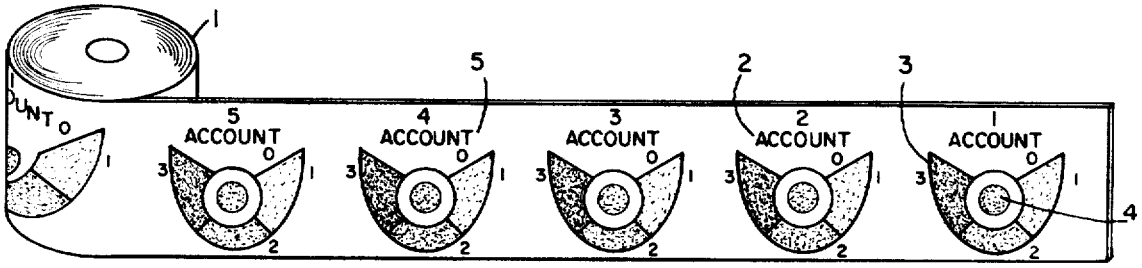
FIG. 2 is the same as FIG. 1 except that it is of elliptical form with a range of "Smoke Spot Number" from 0 to 3.
Figure 3:
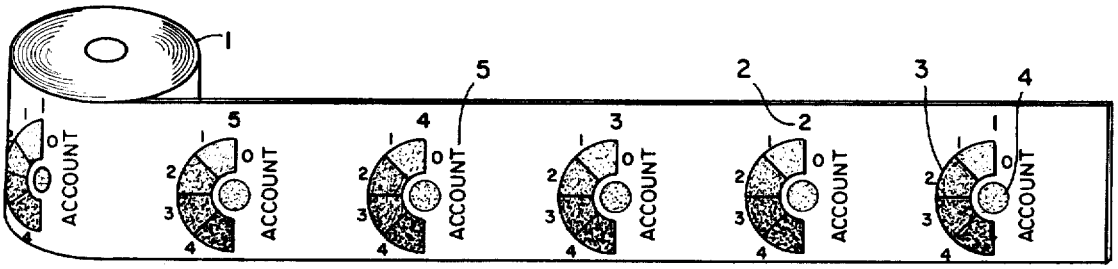
FIG. 3 is the same as FIG. 1 except that it is of crescent form with a range of "Smoke Spot Number" from 0 to [5.] *4.*
Figure 4:
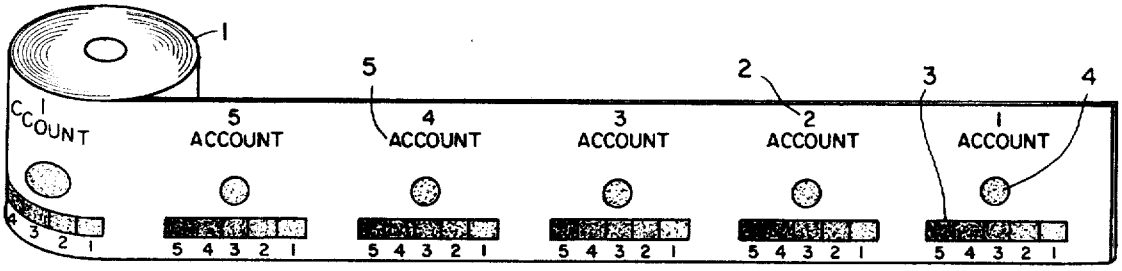
*FIG. 4 is the same as FIG. 1 except that it is of rectangular form with a range of "Smoke Spot Number" from 0 to 5.*

Although the drawings, FIGS. 1,2,3 & 4, show several preferred forms of the invention, it is to be understood that other embodiments may be made which come within the scope and essence of the claims.

I claim:

1. In a filter test paper or the like for use in a sampling and testing of the smoke of an oil burner and for [indicating] *determining* a "Smoke Spot Number" of the smoke content of flue gases when compared to standard gray smoke scales, the [imprint] *improvement* comprising: said [roll of] filter test paper provided with a plurality of evenly spaced repeating calibrated gray smoke scales, each of said gray scales having at least one form of preselected geometrical shapes, each of the gray scale shapes evenly divided into sectors of different "Smoke Spot Number" indicating density, said calibrated gray smoke scales located centrally on said test paper, whereby a sample test smoke spot will appear adjacent to a selected one of the calibrated gray smoke scales during the smoke test and "Smoke Spot Number" content of the flue gas can be visually determined by comparing the sample test smoke spot with said one of the *repeating* calibrated gray smoke scales.

2. A smoke test [roll of test filter paper] *filter test paper or the like* as in claim 1 whereby the geometrical like shapes of the calibrated gray smoke scales may be in circular, elliptical, crescent, or rectangular form.

*3. A smoke test filter test paper or the like as in claim 1 whereby the said smoke test filter test paper or the like may be in roll or length form.*

*4. In a filter test paper or the like for use in a sampling and testing the smoke of an oil burner and for determining a smoke number of the smoke content flue gases when compared to standard gray smoke scales, the improvement comprising: said filter test paper being provided with a plurality of evenly spaced repeating calibrated gray scales, each of said gray scales having at least one form of preselected geometrical shapes, each of the gray scale shapes evenly divided into sectors of different smoke number indicating density, said calibratred gray scales located centrally on said test paper, whereby a smoke sample spot will appear adjacent to a selected one of the calibrated gray scales during the smoke test and smoke number content of the flue gas can be visually determined by comparing the sample smoke spot with said one of the repeating calibrated gray scales.*

*5. A smoke test filter test paper or the like as in claim 4 whereby the geometrical like shapes of the calibrated gray scales may be in circular, elliptical, crescent, or rectangular form.*

*6. A smoke test filter test paper or the like as in claim 4 whereby the said smoke test filter test paper or the like may be in roll or length form.*

* * * * *